(12) United States Patent
Han et al.

(10) Patent No.: US 9,090,551 B1
(45) Date of Patent: Jul. 28, 2015

(54) METHODS OF MAKING FORMIC ACID FROM GLYCEROL

(71) Applicant: King Abdullah University of Science and Technology, Thuwal (SA)

(72) Inventors: Yu Han, Thuwal (SA); Jizhe Zhang, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 14/642,801

(22) Filed: Mar. 10, 2015

Related U.S. Application Data

(60) Provisional application No. 61/970,978, filed on Mar. 27, 2014.

(51) Int. Cl.
| | | |
|---|---|---|
| *C07C 53/00* | (2006.01) | |
| *C07C 51/235* | (2006.01) | |
| *B01J 27/199* | (2006.01) | |
| *C01B 25/45* | (2006.01) | |

(52) U.S. Cl.
CPC ............ *C07C 51/235* (2013.01); *B01J 27/199* (2013.01); *C01B 25/45* (2013.01)

(58) Field of Classification Search
CPC combination set(s) only.
See application file for complete search history.

(56) References Cited

U.S. PATENT DOCUMENTS

2013/0035507 A1\* 2/2013 Zhang et al. .................. 562/538
2013/0245319 A1\* 9/2013 Bosmann et al. ............. 562/531

OTHER PUBLICATIONS

Database Caplus Chemical Abstracts Service, Columbus, Ohio, US; Database Accession No. 1987:644962, Abstract of Tyurin et al., Azerbaidzhanskii Khimicheskii Zhurnal (1986), (5), 93-7.\*
Carrettin et al., Topics in Catalysis vol. 27, Nos. 1-4, Feb. 2004.\*
Prati et al., Top Catal (2009) 52:288-296.\*
Brett et al., Angew. Chem. Int. Ed. 2011, 50, 10136-10139.\*
Sobczak et al., Catalysis Today 158 (2010) 121-129.\*
Zhang et al., RSC Adv., 2014, 4, 35463.\*

\* cited by examiner

*Primary Examiner* — Karl J Puttlitz
(74) *Attorney, Agent, or Firm* — Thomas|Horstemeyer, LLP

(57) ABSTRACT

Embodiments of the present disclosure provide for methods of converting glycerol to formic acid and the like.

17 Claims, 1 Drawing Sheet

Scheme 1

METHODS OF MAKING FORMIC ACID FROM GLYCEROL

CROSS-REFERENCE TO RELATED APPLICATION

This application claims priority to U.S. provisional application entitled "METHODS OF MAKING FORMIC ACID FROM GLYCEROL," having Ser. No. 61/970,978, filed on Mar. 27, 2014, which is entirely incorporated herein by reference.

BACKGROUND

In the context of the future hydrogen economy, effective production of hydrogen ($H_2$) from readily available and sustainable resources is of crucial importance. Thus, there is a need to find alternative processes for forming chemicals that can be used to store and to form $H_2$.

SUMMARY

Embodiments of the present disclosure provide for methods of converting glycerol to formic acid and the like. An embodiment of the present disclosure includes a method, among others, that includes: providing glycerol, a catalyst, and $O_2$; and converting glycerol to formic acid in the presence of a catalyst and $O_2$ at a temperature of about 455 K or less. In an embodiment, the catalyst can be a vanadium-substituted phosphomolybic acid such as $H_{3+n}PV_nMo_{12-n}O_{40}$, wherein n is 1, 2, or 3. In an embodiment, the glycerol is at a concentration of about 40 to 90 wt % in an aqueous solution and the $O_2$ is present in an amount of about 2 MPa to 4 MPa the absolute yield of formic acid is up to about 40 wt %. In an embodiment, the absolute yield of formic acid is up to about 40 wt %. Additional details are provided herein.

BRIEF DESCRIPTION OF THE DRAWINGS

Many aspects of the disclosed methods can be better understood with reference to the following drawings.

DETAILED DESCRIPTION

Figure 1:
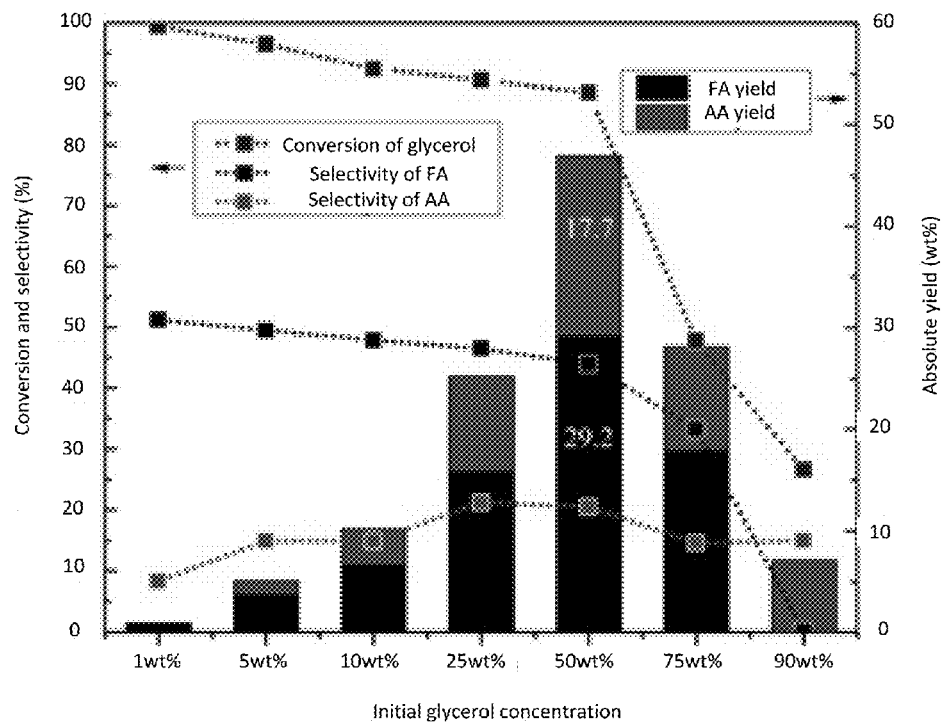
FIG. 1 illustrates a graph of the selective oxidation of glycerol in an aqueous solution over the $H_4PV_1Mo_{11}O_{40}$ catalyst. Reaction conditions: 10 g of glycerol solution with a designated concentration; 0.1 mmol of catalyst; at 423 K and a constant $O_2$ pressure of 2 MPa for 3 h.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in K, and pressure is at or near atmospheric. Standard temperature and pressure are defined as 293 K and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for methods of converting glycerol to formic acid. An advantage of the present disclosure is that glycerol can be selectively converted to formic acid at relatively low temperatures (e.g., about 460 K or less). Another advantage is that the glycerol can be present at highly concentrated levels (e.g., about 90 wt % or less or about 75 wt % or less) to provide a higher conversion efficiency, which can translate into higher potential $H_2$ yields per unit volume.

In an embodiment, glycerol can be selectively oxidized to formic acid in an aqueous solution with molecular oxygen ($O_2$) using a catalyst. In an embodiment, the glycerol, in an aqueous solution, can be at a concentration of about 1 to 90 wt %, about 1 to 75 wt %, about 1 to 50 wt %, about 50 wt %, about 40 to 90 wt %, 40 to 80 wt %, 40 to 70 wt %, or 40 to 60 wt %.

In an embodiment, the conversion rate of glycerol to formic acid can be about 30 to 100% or about 40 to 90%. In an embodiment, the absolute yield of formic acid can be up to about 40 wt %, up to about 37 wt %, about 10 to 40 wt % or about 10 to 37 wt %. In an embodiment, the selectivity for formic acid can be about 40 to 60% or about 50%.

In an embodiment, the catalyst can be a vanadium-substituted phosphomolydic acid catalyst or its salt form. In an embodiment, the vanadium-substituted phosphomolydic acid catalyst can have the following formula: $H_{3+n}PV_nMo_{12-n}O_{40}$ (n=1, 2, or 3) and the corresponding salt form would have a similar formula. In an embodiment, the catalyst can be $H_6PV_3Mo_9O_{40}$, $H_6PV_3Mo_9O_{40}$, or $H_4PV_1Mo_{11}O_{40}$. In an embodiment, the catalyst can have a concentration of about 1 to 5 wt % or 2-5 wt % in the aqueous solution.

In an embodiment, the reaction can be conducted in a reactor or similarly appropriate apparatus or system. For example, glycerol can be added to the reactor with the catalyst. The reactor can be heated to a desired temperature for a certain time frame. $O_2$ can be introduced to the reactor and maintained at a desired amount. In an embodiment, the temperature of the reactor can be about 460 K or less or about 400 to 455 K. In an embodiment, the reaction time can be about 2 to 5 hours. In an embodiment, the $O_2$ can be present in the reactor at about 2 MPa to 4 MPa. One or more of the variables (e.g., amount of glycerol, type and/or amount of catalyst, amount of $O_2$, the temperature, the pressure, and the like) can be adjusted as needed depending of one or more of the other variables in an effort to achieve the desired conversion rate. Once the reaction is complete or during the reaction, the formic acid can be removed from the reactor.

EXAMPLE

Now having described the embodiments of the present disclosure, in general, the Example describes some additional embodiments of the present disclosure. While embodiments of present disclosure are described in connection with the Example and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Brief Introduction

Formic acid is an important commodity chemical as well as a promising medium for hydrogen storage and hydrogen production. In this example, we report that formic acid can be produced through selective oxidation of glycerol, a low-cost by-product of biodiesel, by using vanadium-substituted phosphomolybdic acids as catalysts and molecular oxygen as the oxidant.

Significantly, this catalytic system allows for high-concentration conversions and thus leads to exceptional efficiency. Specifically, 3.64 g of formic acid was produced from a 10 g of glycerol/water (50/50 in weight) solution.

Discussion

In the context of the future hydrogen economy, effective production of hydrogen ($H_2$) from readily available and sustainable resources is of crucial importance.[1,2] Currently, $H_2$ is mainly produced from nonrenewable natural gases, petroleum and coal through reforming process, while technologies for producing $H_2$ from water by solar energy are not yet mature.[3] The possibility of generating $H_2$ from biomass that is both abundant and ecologically sustainable has attracted substantial research efforts in the last decade, and various technologies have been developed including fermentation,[4] enzymatic conversion,[5,6] gasification,[7] and steam/aqueous reforming.[8,9] However, high-yield, low-cost production of $H_2$ from biomass remains a challenge. As a traditional commodity chemical in high demand in the chemical, pharmaceutical and agricultural industries, formic acid (FA) has recently received particular attention because it was demonstrated to be an efficient storage medium for $H_2$.[10-12] With the development of new processes that allow selective decomposition of FA into $H_2$ and $CO_2$,[13-21] it is also possible to consider FA as a precursor to hydrogen production, although this is economically and ecologically meaningful only when FA can be produced from renewable feedstock using low-cost processes.

Figure 2:
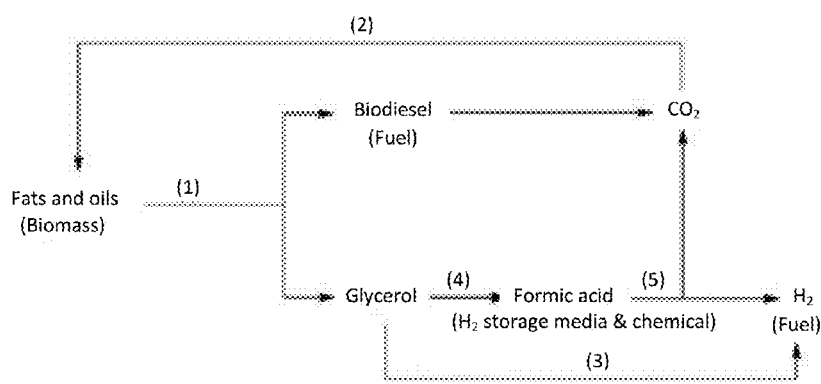
FIG. 2 illustrates Scheme 1, which is a schematic illustration of the renewable fuel concept based on biomass conversion: (1) triglyceride transesterification; (2) photosynthesis; (3) aqueous/gas phase reforming; (4) catalytic oxidation; and (5) dehydrogenation of FA.

The significantly increased global demand for biodiesel results in the large surplus of glycerol, the main byproduct in manufacturing biodiesel fuels by the triglyceride transesterification process. As a consequence, the price of glycerol has dropped markedly in the last 10 years and it will certainly fall further along with the increase of biodiesel production. This makes glycerol a promising feedstock to be converted to various high-valued products.[22-24] On the other hand, the use of glycerol to produce $H_2$ would fully integrate biodiesel into the renewable fuel concept, considering that in addition to itself, the $H_2$ obtained from its by-product is also a clean fuel (FIG. 2, Scheme 1).[8, 25-28] Hydrogen generation from glycerol has been investigated mainly by means of aqueous phase reforming (APR).[29-31] A major challenge in APR of glycerol is to achieve a high selectivity for $H_2$. Due to a series of parallel reactions, the products always contain small amounts of CO and light alkanes (e.g., methane and ethane) in the gas phase as well as glycerol derivatives such as C1-C3 alcohols and acids in the liquid phase. Another issue is that the APR process can only be applied to very diluted (~1%) aqueous solutions.[8, 26] Less studied is gas phase reforming of glycerol, which requires high reaction temperatures (>773 K) and suffers from low yields of $H_2$ as well as coke formation that causes deactivation of the catalyst.[25, 28] Processes that enable selective reforming of concentrated glycerol solutions at low temperatures remain to be developed.

Here, we report that glycerol can be selectively oxidized to FA in an aqueous solution with molecular oxygen by using vanadium-substituted phosphomolybdic acids as catalysts. Given that many efficient catalytic systems have been developed for dehydrogenating FA to generate $H_2$, the selective conversion of glycerol to FA offers an alternative route to the direct extraction of $H_2$ from glycerol (Scheme 1). In comparison with conventional APR processes, this catalytic system requires a lower temperature (423 K) and leads to higher selectivity; more importantly, it can work with highly concentrated aqueous solutions of glycerol (up to 75 wt %) to give rise to much higher conversion efficiencies, i.e., higher potential $H_2$ yields per unit volume of the reactor. The liquid product FA also holds advantages over $H_2$ for its ease of storage and transportation and its readiness to release $H_2$ when needed.

In our recent studies, we have demonstrated that many Keggin-type heteropoly acids (HPAs) can effectively convert biomass substrates under oxidative conditions due to their strong Brönsted acidity, while the reaction pathway is largely determined by the type of addenda atom in the HPA catalyst.[32-34] For example, we reported the direct conversion of cellulose to glycolic acid with high yields (about 50%) using molecular oxygen in a water medium in which a phosphomolybdic acid ($H_3PMo_{12}O_{40}$) acts as a bi-functional catalyst to catalyze both the hydrolysis of cellulose and the subsequent oxidation reactions. Further study indicated that the product selectivity of this system changed from glycolic acid to FA if some molybdenum (Mo) atoms in the $H_3PMo_{12}O_{40}$ catalyst were substituted by vanadium (V).[34] Similar results were also reported by other research groups[35-37] and were attributed to the selective oxidative cleavage of C—C bonds by the V atoms in HPA. We used vanadium-substituted phosphomolybdic acids ($H_{3+n}PV_nMo_{12-n}O_{40}$) as catalysts to convert glycerol through oxidation. The reactions were carried out at 423 K for 3 hours under 2 MPa-4 MPa $O_2$ in a Teflon-lined stainless autoclave reactor (75 mL) that contained 10 g of an aqueous solution of glycerol with a designated concentration and 0.1 mmol of catalyst.

We first used mono-V-substituted phosphomolybdic acid ($H_4PV_1Mo_{11}O_{40}$) to convert glycerol in aqueous solutions of different concentrations ranging from 1 wt % to 90 wt %. Full conversion of glycerol was achieved in the 1 wt % solution with three major products detected in the liquid phase, including FA (selectivity: 51.2%), acetic acid (selectivity: 8.3%), and formaldehyde (selectivity: 7.2%), while the only product detected in the gas phase was $CO_2$. When a 5 wt % glycerol solution was used for conversion, 98% of the glycerol was converted with nearly unchanged product selectivities. However, it is worth noting that the absolute yields of the products, which are defined as their weight percentages relative to the initial reaction mixture, were markedly increased in this case due to the five times higher substrate concentration (FIG. 1). Further increasing the concentration of the glycerol substrate resulted in gradually decreased conversion, disappearance of formaldehyde in the products, and continuously increased absolute yields of FA and acetic acid (AA). As shown in FIG. 1, the maximum absolute yields (29.2 wt % for FA and 17.7 wt % for AA) were obtained in the system that initially contained 50 wt % of glycerol. These values are exceptionally high, considering that conventional oxidative biomass conversion reactions are usually performed in diluted solutions (<5 wt %).[38-40] With the initial glycerol concentration exceeding 50 wt %, the conversion as well as the selectivity of FA dramatically decreased, giving rise to lower absolute yields of FA (FIG. 1). When a 90 wt % glycerol solution was used in the reaction, for example, the conversion of glycerol was 25% and AA was the only detectable product in the liquid phase (FIG. 1). These results suggest that higher water content in the reaction system favors the formation of FA. We note that glycerol has been converted through selective oxidation to various high-value chemicals, such as glyceric acid,[41] tartronic acid,[42,43] ketomalonic acid,[44] and dihydroxyacetone[45,46], and that the use of HPAs to catalyze the dehydration of glycerol to acrolein[47-49] or glycerol acetylation[50] has also been reported. However, to the best of our knowledge, conversion of glycerol to FA with such a high selectivity and efficiency has never been achieved prior to this study. Notably, the yield of AA, another useful chemical with important applications, is also remarkable in this system.

We found that the conversion efficiency of glycerol to FA can be further enhanced by increasing the vanadium content in the phosphovanadomolybdic catalyst. Under identical reaction conditions, multi-V-substituted phosphomolybdic acid catalysts ($H_5PV_2W_{12}O_{40}$ and $H_6PV_3Mo_9O_{40}$) gave rise to more FA and less AA than their mono-substituted counterpart. The FA selectivity increases in the following order: $H_6PV_3Mo_9O_{40} > H_5PV_2W_{12}O_{40} > H_4PV_1MO_{11}O_{40}$, and this trend applies to both concentrated (50 wt %) and diluted (1 wt %) glycerol solutions (Table 1). The highest absolute yield of FA (36.4 wt %), which corresponds to a selectivity of 51.3% from the 50 wt % glycerol solution, was achieved by $H_6PV_3Mo_9O_{40}$ (Table 1). The fact that the V-free phosphomolybdic acid is catalytically inactive under the same reaction conditions (Table 1) further demonstrates the role of vanadium in this reaction.

TABLE 1

Oxidative conversions of various substrates catalyzed by V-substituted phosphomolybdic acids[a]

| Catalysts | Substrate | Conc. (wt %) | Conversion (%) | Selectivity (%) FA | AA |
|---|---|---|---|---|---|
| $HPMoV_1$[a] | Glycerol | 50 | 90.6 | 41.2 | 19.2 |
| $HPMoV_2$[a] | glycerol | 50 | 93.0 | 48.5 | 13.0 |
| $HPMoV_3$[a] | glycerol | 50 | 94.8 | 51.3 | 11.2 |
| $HPMoV_1$[b] | glycerol | 1 | 99.5 | 51.2 | 8.3 |
| $HPMoV_2$[b] | glycerol | 1 | 100 | 55.2 | 2.9 |
| $HPMoV_3$[b] | glycerol | 1 | 100 | 60.0 | 2.8 |
| $HPMo$[b] | glycerol | 1 | — | — | — |
| $HPMoV_1$[b] | Lactic acid | 1 | 100 | 7.4 | 38.2 |
| $HPMoV_1$[c] | methanol | 1 | 5.8 | 5.2 | — |
| $HPMoV_1$[c] | formaldehyde | 1 | 43.9 | 83.8 | — |
| $HPMoV_1$[b] | formic acid | 50 | 4.7 | — | — |

[a]Reaction conditions: 10 g aqueous solution of the substrate with a designated concentration; 0.1 mmol of catalyst; for 3 h;
[a]423 K and 4 MPa $O_2$;
[b]423 K and 2 MPa $O_2$;
[c]453 K and 2 MPa $O_2$.

The oxidative C—C bond cleavage of primary alcohol and vicinal diols catalyzed by $H_5PV_2W_{12}O_{40}$ was believed to follow an electron transfer and oxygen transfer (ET-OT) reaction mechanism.[51] Meanwhile, previous studies suggested that in the conversion of glucose to FA catalyzed by $H_5PV_2W_{12}O_{40}$, the intermediates are aldehyde-group-containing compounds and there is more than one mechanism involved in the reaction.[35, 37] A recent study of the use of an AuPd/$TiO_2$ catalyst for selective oxidation of glycerol proposed that FA and AA were generated through the oxidative decomposition of lactic acid, which was the major product of that system.[52] In our system, we found that lactic acid can indeed be converted to FA and AA with high selectivities (7.4% and 38.2%, respectively) (Table 1). On the other hand, when methanol and formaldehyde were used as the substrates, slower conversions with lower FA yields were observed, as compared with the cases of glycerol (Table 1). This result excludes methanol or formaldehyde from being the intermediates for the production of FA in this system. However, the exact reaction pathway of selective oxidation of glycerol to FA and AA over vanadium-substituted phosphomolybdic acids remains unclear, due to the complexity of this reaction. We also investigated the stability of FA in this catalytic system by using FA (50 wt % in water) as the substrate, and found that only ~5% of FA was decomposed under the reaction conditions. This result reveals that FA is rather stable in this system. Therefore, the $CO_2$ produced in this reaction is not from the dehydrogenation of FA, as supported by the observation that varying the glycerol/catalyst ratio did not much change the selectivity of FA (FIG. 1). In addition, we can conclude from this result that the absence of FA in the products of high concentration (e.g., 90 wt %) glycerol conversion is not due to its decomposition but more likely associated with the low water content in the reaction system.

CONCLUSIONS

We demonstrated that V-substituted phosphomolybdic acid catalysts enable the selective oxidation of glycerol to formic acid in highly concentrated aqueous solutions using molecular oxygen. The preliminary results show that the absolute yield of formic acid could reach 36.4 wt % of the initial reaction mixture, representing exceptionally high conversion efficiency. This reaction provides an alternative route to the production of $H_2$ from glycerol, given that formic acid can be readily and selectively converted to $H_2$. In comparison with conventional reforming processes, this process requires lower energy input while offering higher selectivity and yield. Taking advantage of the large surplus of glycerol, it fully integrates biodiesel in the renewable fuel concept. A noteworthy advantage of the HPA catalysts used in this example is that they can be recovered in solid form after reactions by distilling the products and solvent out and reused.

REFERENCES

1. A. A. Evers, the Hydrogen Society, *Hydrogeit Verlag*, 2012.
2. J. Rifkin, the Hydrogen Economy, *Penguin Putnam Inc.*, 2002.
3. A. J. Esswein and D. G. Nocera, *Chem Rev*, 2007, 107, 4022-4047.
4. T. A. Ngo, T. H. Nguyen and T. V. B. Ha, *Renew Energ*, 2012, 37, 174-179.
5. J. S. Martin del Campo, J. Rollin, S. Myung, Y. Chun, S. Chandrayan, R. Patino, M. W. W. Adams and Y. H. P. Zhang, *Angew Chem Int Edit*, 2013, 52, 4587-4590.
6. J. Woodward, M. Orr, K. Cordray and E. Greenbaum, *Nature*, 2000, 405, 1014-1015.
7. D. Castello and L. Fiori, *Bioresource Technol*, 2011, 102, 7574-7582.
8. P. R. de la Piscina and N. Homs, *Chem Soc Rev*, 2008, 37, 2459-2467.
9. R. D. Cortright, R. R. Davda and J. A. Dumesic, *Nature*, 2002, 418, 964-967.
10. F. Joo, *Chemsuschem*, 2008, 1, 805-808.
11. B. Zaidman, H. Wiener and Y. Sasson, *Int J Hydrogen Energ*, 1986, 11, 341-347.
12. R. Williams, R. S. Crandall and A. Bloom, *Appl Phys Lett*, 1978, 33, 381-383.
13. S. Zhang, O. Metin, D. Su and S. H. Sun, *Angew Chem Int Edit*, 2013, 52, 3681-3684.
14. Z.-L. Wang, J.-M. Yan, Y. Ping, H.-L. Wang, W.-T. Zheng and Q. Jiang, *Angewandte Chemie International Edition*, 2013, 52, 4406-4409.
15. Y. Y. Cai, X. H. Li, Y. N. Zhang, X. Wei, K. X. Wang and J. S. Chen, *Angew Chem Int Edit*, 2013, 52, 11822-11825.
16. Q. Y. Bi, X. L. Du, Y. M. Liu, Y. Cao, H. Y. He and K. N. Fan, *J Am Chem Soc*, 2012, 134, 8926-8933.
17. K. Tedsree, T. Li, S. Jones, C. W. A. Chan, K. M. K. Yu, P. A. J. Bagot, E. A. Marquis, G. D. W. Smith and S. C. E. Tsang, *Nat Nanotechnol*, 2011, 6, 302-307.
18. M. Ojeda and E. Iglesia, *Angew Chem Int Edit*, 2009, 48, 4800-4803.
19. X. C. Zhou, Y. J. Huang, W. Xing, C. P. Liu, J. H. Liao and T. H. Lu, *Chem Commun*, 2008, 3540-3542.
20. B. Loges, A. Boddien, H. Junge and M. Beller, *Angew Chem Int Edit*, 2008, 47, 3962-3965.
21. C. Fellay, P. J. Dyson and G. Laurenczy, *Angew Chem Int Edit*, 2008, 47, 3966-3968.
22. E. Arceo, P. Marsden, R. G. Bergman and J. A. Ellman, *Chem Commun*, 2009, 3357-3359.
23. C. H. C. Zhou, J. N. Beltramini, Y. X. Fan and G. Q. M. Lu, *Chem Soc Rev*, 2008, 37, 527-549.
24. M. Pagliaro, R. Ciriminna, H. Kimura, M. Rossi and C. Della Pina, *Angew Chem Int Edit*, 2007, 46, 4434-4440.
25. S. Adhikari, S. Fernando and A. Haryanto, *Catal Today*, 2007, 129, 355-364.
26. G. W. Huber and J. A. Dumesic, *Catal Today*, 2006, 111, 119-132.
27. G. W. Huber, J. W. Shabaker and J. A. Dumesic, *Science*, 2003, 300, 2075-2077.
28. S. Czernik, R. French, C. Feik and E. Chornet, *Ind Eng Chem Res*, 2002, 41, 4209-4215.
29. P. V. Tuza, R. L. Manfro, N. F. P. Ribeiro and M. M. V. M. Souza, *Renew Energ*, 2013, 50, 408-414.
30. P. J. Dietrich, T. P. Wu, A. Sumer, J. A. Dumesic, J. Jellinek, W. N. Delgass, F. H. Ribeiro and J. T. Miller, *Top Catal*, 2013, 56, 1814-1828.
31. D. L. King, L. A. Zhang, G. Xia, A. M. Karim, D. J. Heldebrant, X. Q. Wang, T. Peterson and Y. Wang, *Appl Catal B-Environ*, 2010, 99, 206-213.
32. J. Z. Zhang, X. Liu, M. Sun, X. H. Ma and Y. Han, *Acs Catal*, 2012, 2, 1698-1702.
33. J. Z. Zhang, X. Liu, M. N. Hedhili, Y. H. Zhu and Y. Han, *Chemcatchem*, 2011, 3, 1294-1298.
34. J. Zhang, M. Sun, X. Liu and Y. Han, *Catal Today*. http://dx.doi.orq/10.1016/j.cattod.2013.12.010
35. J. Li, D. J. Ding, L. Deng, Q. X. Guo and Y. Fu, *Chemsuschem*, 2012, 5, 1313-1318.
36. J. Albert, R. Wolfel, A. Bosmann and P. Wasserscheid, *Energ Environ Sci*, 2012, 5, 7956-7962.
37. R. Wolfel, N. Taccardi, A. Bosmann and P. Wasserscheid, *Green Chem*, 2011, 13, 2759-2763.
38. G. L. Brett, Q. He, C. Hammond, P. J. Miedziak, N. Dimitratos, M. Sankar, A. A. Herzing, M. Conte, J. A. Lopez-Sanchez, C. J. Kiely, D. W. Knight, S. H. Taylor and G. J. Hutchings, *Angew Chem Int Edit*, 2011, 50, 10136-10139.
39. A. Villa, G. M. Veith and L. Prati, *Angew Chem Int Edit*, 2010, 49, 4499-4502.
40. R. M. Painter, D. M. Pearson and R. M. Waymouth, *Angew Chem Int Edit*, 2010, 49, 9456-9459.
41. S. Carrettin, P. McMorn, P. Johnston, K. Griffin and G. J. Hutchings, *Chem Commun*, 2002, 696-697.
42. B. Katryniok, H. Kimura, E. Skrzynska, J. S. Girardon, P. Fongarland, M. Capron, R. Ducoulombier, N. Mimura, S. Paul and F. Dumeignil, *Green Chem*, 2011, 13, 1960-1979.
43. C. L. Bianchi, P. Canton, N. Dimitratos, F. Porta and L. Prati, *Catal Today*, 2005, 102, 203-212.
44. R. Ciriminna and M. Pagliaro, *Adv Synth Catal*, 2003, 345, 383-388.
45. S. Hirasawa, H. Watanabe, T. Kizuka, Y. Nakagawa and K. Tomishige, *J Catal*, 2013, 300, 205-216.
46. Y. Kwon, Y. Birdja, I. Spanos, P. Rodriguez and M. T. M. Koper, *Acs Catal*, 2012, 2, 759-764.
47. B. Katryniok, S. Paul, M. Capron, V. Belliere-Baca, P. Rey and F. Dumeignil, *Chemsuschem*, 2012, 5, 1298-1306.
48. M. H. Haider, N. F. Dummer, D. Z. Zhang, P. Miedziak, T. E. Davies, S. H. Taylor, D. J. Willock, D. W. Knight, D. Chadwick and G. J. Hutchings, *J Catal*, 2012, 286, 206-213.
49. B. Katryniok, S. Paul, M. Capron and F. Dumeignil, *Chemsuschem*, 2009, 2, 719-730.
50. P. Ferreira, I. M. Fonseca, A. M. Ramos, J. Vital and J. E. Castanheiro, *Appl Catal B-Environ*, 2009, 91, 416-422.
51. A. M. Khenkin and R. Neumann, *J Am Chem Soc*, 2008, 130, 14474-14476.
52. J. L. Xu, H. Y. Zhang, Y. F. Zhao, B. Yu, S. Chen, Y. B. Li, L. D. Hao and Z. M. Liu, *Green Chem*, 2013, 15, 1520-1525.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to figures and the measurement techniques. In addition, the phrase "about 'x' to 'y'" includes "about 'x' to about 'y'". When a range includes "zero" and is modified by "about" (e.g., about one to zero or about zero to one), about zero can include, 0, 0.1. 0.01, or 0.001.

While only a few embodiments of the present disclosure have been shown and described herein, it will become apparent to those skilled in the art that various modifications and changes can be made in the present disclosure without departing from the spirit and scope of the present disclosure. All such modification and changes coming within the scope of the appended claims are intended to be carried out thereby.

We claim:

1. A method, comprising:
providing glycerol, a catalyst, and $O_2$; and
converting glycerol to formic acid in the presence of a catalyst and $O_2$ at a temperature of about 455 K or less, wherein the catalyst is a vanadium-substituted phosphomolybic acid.

2. The method of claim 1, wherein the catalyst is $H_{3+n}PV_nMo_{12-n}O_{40}$, wherein n is 1, 2, or 3.

3. The method of claim 2, wherein the catalyst is at a concentration of about 1 to 5 wt %.

4. The method of claim 1, wherein:
the catalyst is a vanadium-substituted phosphomolybic acid;
the catalyst is at a concentration of about 1 to 5 wt %; and
wherein the absolute yield of formic acid is up to about 40 wt %.

5. The method of claim 1, wherein the glycerol is at a concentration of about 40 to 90 wt % in an aqueous solution.

6. The method of claim 1, wherein the temperature is about 400 to 455 K.

7. The method of claim 1, wherein the $O_2$ is present in an amount of about 2 MPa to 4 MPa.

8. The method of claim 1, wherein the catalyst is $H_{3+n}PV_nMo_{12-n}O_{40}$, wherein n is 1, 2, or 3, wherein the catalyst is at a concentration of about 1 to 5 wt %, wherein the glycerol is at a concentration of about 40 to 90 wt % in an aqueous solution, wherein the temperature is about 400 to 455 K, and wherein the $O_2$ is present in an amount of about 2 MPa to 4 MPa.

9. The method of claim 1, wherein the catalyst is $H_6PV_3Mo_9O_{40}$.

10. The method of claim 1, wherein the catalyst is $H_4PV_1Mo_{11}O_{40}$.

11. The method of claim 4, wherein the glycerol is at a concentration of about 40 to 90 wt % in an aqueous solution.

12. The method of claim 1, wherein the temperature is about 400 to 455 K.

13. The method of claim 2, wherein the $O_2$ is present in an amount of about 2 MPa to 4 MPa.

14. The method of claim 2, wherein the $O_2$ is present in an amount of about 2 MPa to 4 MPa.

15. The method of claim 3, wherein the $O_2$ is present in an amount of about 2 MPa to 4 MPa.

16. The method of claim 8, wherein the catalyst is $H_6PV_3Mo_9O_{40}$.

17. The method of claim 8, wherein the catalyst is $H_4PV_1Mo_{11}O_{40}$.

* * * * *